(12) United States Patent
Ellington et al.

(10) Patent No.: US 10,918,484 B2
(45) Date of Patent: Feb. 16, 2021

(54) CONTINUOUS COMPRESSION FIXATION DEVICE FOR THE FUSION OF AN INTERCALARY STRUCTURAL AUGMENT

(71) Applicant: PRESSIO, INC., Atlanta, GA (US)

(72) Inventors: John Kent Ellington, Charlotte, NC (US); Daniel Leas, Huntersville, NC (US)

(73) Assignee: PRESSIO, INC., Atlanta, GA (US)

( * ) Notice: Subject to any disclaimer, the term of this patent is extended or adjusted under 35 U.S.C. 154(b) by 0 days.

(21) Appl. No.: 15/919,829

(22) Filed: Mar. 13, 2018

(65) Prior Publication Data
US 2019/0282365 A1    Sep. 19, 2019

(51) Int. Cl.
| A61F 2/28 | (2006.01) |
| A61B 17/68 | (2006.01) |
| A61F 2/30 | (2006.01) |
| A61F 2/44 | (2006.01) |
| A61B 17/064 | (2006.01) |
| A61B 17/00 | (2006.01) |

(52) U.S. Cl.
CPC ........ *A61F 2/2846* (2013.01); *A61B 17/0642* (2013.01); *A61F 2/447* (2013.01); *A61B 2017/00867* (2013.01); *A61B 2017/0641* (2013.01); *A61B 2017/0645* (2013.01); *A61B 2017/0647* (2013.01); *A61B 2017/681* (2013.01); *A61F 2002/285* (2013.01); *A61F 2002/30092* (2013.01)

(58) Field of Classification Search
CPC ..... A61F 2/2846; A61F 2/447; A61B 17/0642
See application file for complete search history.

(56) References Cited

U.S. PATENT DOCUMENTS

| 6,336,928 B1 * | 1/2002 | Guerin | A61B 17/7059 606/282 |
| 8,979,927 B2 * | 3/2015 | Huntsman | A61F 2/4455 623/17.11 |
| 2006/0058802 A1 * | 3/2006 | Kofoed | A61B 17/0642 606/75 |
| 2008/0319443 A1 * | 12/2008 | Focht | A61B 17/0642 606/75 |
| 2011/0118842 A1 * | 5/2011 | Bernard | A61B 17/0642 623/17.11 |
| 2013/0231667 A1 * | 9/2013 | Taylor | A61B 17/8085 606/75 |

(Continued)

*Primary Examiner* — Tessa M Matthews
(74) *Attorney, Agent, or Firm* — Morris, Manning & Martin, LLP; Bryan D. Stewart

(57) ABSTRACT

A continuous compression fixation device for coupling a first bony structure to a second bony structure, including: a body structure; and a plurality of arm structures extending from the body structure, wherein at least one of the plurality of arm structures is configured to be coupled to the first bony structure and at least one opposed one of the plurality of arm structures is configured to be coupled to the second bony structure; wherein the body structure and the plurality of arm structures are manufactured from a shape memory material; and wherein tips of the at least one of the plurality of arm structures and the at least one opposed one of the plurality of arm structures are biased towards one another such that a desired compressive force is applied to an intercalary structural augment disposed between the first bony structure and the second bony structure.

11 Claims, 6 Drawing Sheets

(56) References Cited

U.S. PATENT DOCUMENTS

| | | | |
|---|---|---|---|
| 2014/0214037 A1* | 7/2014 | Mayer | A61B 17/0642 606/75 |
| 2014/0309639 A1* | 10/2014 | Averous | A61B 17/0642 606/75 |
| 2015/0230839 A1* | 8/2015 | Riccione | A61B 17/8014 606/297 |
| 2015/0313592 A1* | 11/2015 | Coillard-Lavirotte | A61B 17/0642 606/75 |
| 2016/0135808 A1* | 5/2016 | Anderson | A61B 17/0644 606/219 |
| 2017/0209193 A1* | 7/2017 | Hartdegen | A61B 17/808 |
| 2018/0008263 A1* | 1/2018 | Goldstein | A61B 17/0642 |
| 2018/0353172 A1* | 12/2018 | Hartdegen | A61B 17/0682 |
| 2019/0105040 A1* | 4/2019 | Gordon | A61B 17/0642 |

\* cited by examiner

CONTINUOUS COMPRESSION FIXATION DEVICE FOR THE FUSION OF AN INTERCALARY STRUCTURAL AUGMENT

FIELD OF THE INVENTION

The present invention relates generally to a continuous compression fixation device for the fusion of an intercalary structural augment. More specifically, the present invention relates to a continuous compression fixation device, such as a surgical staple or the like, manufactured from a metallic or non-metallic shape memory material, such as nitinol (i.e. nickel-titanium) or the like, for the fusion of an intercalary structural augment, such as an intervertebral cage and/or bone graft in an intervertebral fusion, for example. The continuous compression fixation device of the present invention finds applicability in any bony structure fixation application in which restraint of rotational displacement and continuous compressive force are both desired, especially when an intercalary structural augment is present between the adjoined bony structures (e.g. foot, ankle, lower extremity, upper extremity, hand, craniomaxofacial, etc. applications) In the intervertebral fusion, for example, the continuous compression fixation device advantageously provides continuous compressive force over the middle column of the vertebral axis. Multiple levels of instrumentation are also contemplated herein.

BACKGROUND OF THE INVENTION

In intervertebral fusion, for example, intervertebral structural augmentation after discectomy for spinal column decompression and subsequent fusion has long been a preferred procedure. Such intervertebral structural augments have varied from autologous free-fibular strut grafts to allografts to metallic cages to synthetic cages with spaces for bone grafts that increase the rate of fusion. Additional stabilizing instrumentation has also been found to increase the rate of fusion. The mainstays of such stabilizing instrumentation include anterior cervical plates coupled to the anterior or front column of the vertebral axis, lateral lumbar plates, and rod-screw constructs coupled to the posterior or back column of the vertebral axis, for example. Each of these modalities provides rigid fixation and minimizes motion and settling, however none of the modalities provides continuous compression, especially across the associated intervertebral structural augment over the middle column of the vertebral axis. Some of the modalities allow for a predetermined amount of compressive force to be applied initially via mechanical constructs, but this compressive force is diminished with time as settling and/or remodeling of the vertebral endplates occur. A similar situation exists in other anatomical applications.

Direct bony compression has long been identified as critical to achieving primary bone healing and arthrodesis for fusions. This direct bony compression allows for cutting cone bone formation in the absence of the micro-motion that occurs with non-rigid fixation. In foot and ankle surgery, for example, shape memory alloy staples have been utilized with marked success by providing direct bone-to-bone osteosynthesis. However, such shape memory alloy staples do not properly allow for intercalary structural augments and do not correspondingly apply continuous compressive force in the right place(s). The continuous compression fixation device of the present invention remedies these shortcomings.

In general, osseous fusion depends on three distinct physical conditions: bony apposition, strain/stability, and pressure. For primary bone-to-bone healing, these physical conditions allow for new osteon formation through cutting cones and Haversian remodeling. The spine presents a unique environment for iatrogenic fusion. Patients whose pathology dictates an intervertebral fusion mass in their treatment algorithm undergo preparation of the vertebral endplates to accept an intercalary structural augment, again typically consisting of an autologous free-fibular strut graft to a synthetic cage with a space for a bone graft that increases the rate of fusion. Once a graft is placed, for example, a surgeon has the option of instrumenting the fusion or leaving it as is in an in-situ fashion. Again, such instrumentation typically includes anterior cervical plates coupled to the anterior or front column of the vertebral axis, lateral lumbar plates, and rod-screw constructs coupled to the posterior or back column of the vertebral axis, for example. Each of these modalities provides rigid fixation and minimizes motion and settling, however none the modalities provides continuous compression, especially across the associated intervertebral structural augment over the middle column of the vertebral axis. Existing shape memory alloy staples designed for foot and ankle applications do not properly allow for intercalary structural augments and do not correspondingly apply continuous compressive force in the right place(s). Again, the continuous compression fixation device of the present invention remedies these shortcomings.

BRIEF SUMMARY OF THE INVENTION

In various exemplary embodiments, the present invention provides a continuous compression fixation device, such as a surgical staple or the like, manufactured from a metallic or non-metallic shape memory material, such as nitinol (i.e. nickel-titanium) or the like, for the fusion of an intercalary structural augment, such as an intervertebral cage and/or bone graft in an intervertebral fusion, for example. The continuous compression fixation device of the present invention finds applicability in any bony structure fixation application in which restraint of rotational displacement and continuous compressive force are both desired, especially when an intercalary structural augment is present between the bony structures. This includes, but is not limited to, opening wedge osteotomies with tri-cortical auto/allograft and/or deformity correction with intercalary structural augmentation. In intervertebral fusion, for example, the continuous compression fixation device advantageously provides continuous compressive force over the middle column of the vertebral axis. Multiple levels of instrumentation are also contemplated herein.

In one exemplary embodiment, the present invention provides a continuous compression fixation device for coupling a first bony structure to a second bony structure, including: a body structure; and a plurality of arm structures coupled to and extending from the body structure, wherein at least one of the plurality of arm structures is configured to be coupled to the first bony structure and at least one opposed one of the plurality of arm structures is configured to be coupled to the second bony structure; wherein the body structure and the plurality of arm structures are manufactured from a shape memory material; and wherein tips (and other portions) of the at least one of the plurality of arm structures and the at least one opposed one of the plurality of arm structures are biased towards one another relative to a perpendicular orientation with respect to the body structure thereby providing a compressive force between the first bony structure and the second bony structure. Preferably, the tips (and other portions) of the at least one of the plurality of arm structures and the at least one opposed one of the plurality of arm structures are biased towards one another relative to the perpendicular orientation with respect to the body structure such that a desired compressive force is applied to an intercalary structural augment disposed between the first bony structure and the second bony structure. The tips of the at least one of the plurality of arm structures and the at least one opposed one of the plurality of arm structures are configured to be deflected away from one another prior to being coupled to the first bony structure and the second bony structure, respectively. Optionally, the continuous compression fixation device further includes an additional arm structure and an additional opposed arm structure coupled to and extending from the body structure, wherein tips of the additional arm structure and the additional opposed arm structure are biased towards one another relative to the perpendicular orientation with respect to the body structure thereby also providing the compressive force between the first bony structure and the second bony structure. The tips of the at least one of the plurality of arm structures and the at least one opposed one of the plurality of arm structures are biased towards one another relative to the perpendicular orientation with respect to the body structure by a compressive force generated in a proximity of where each of the arm structures and the body structure are coupled. Optionally, the shape memory material includes a shape memory alloy. Optionally, the shape memory alloy includes nitinol. Each of the plurality of arm structures includes a tapered tip such that it may be disposed in a hole drilled into the associated bony structure. Each of the plurality of arm structures further includes one or more friction structures such that it is securely retained in the hole drilled into the associated bony structure. Optionally, the body structure is coupled to the intercalary structural augment disposed between the first bony structure and the second bony structure.

In another exemplary embodiment, the present invention provides a method for providing a continuous compression fixation device for coupling a first bony structure to a second bony structure, including: providing a body structure; providing a plurality of arm structures coupled to and extending from the body structure, wherein at least one of the plurality of arm structures is configured to be coupled to the first bony structure and at least one opposed one of the plurality of arm structures is configured to be coupled to the second bony structure; wherein the body structure and the plurality of arm structures are manufactured from a shape memory material; and wherein tips (and other portions) of the at least one of the plurality of arm structures and the at least one opposed one of the plurality of arm structures are biased towards one another relative to a perpendicular orientation with respect to the body structure thereby providing a compressive force between the first bony structure and the second bony structure; deflecting the tips of the at least one of the plurality of arm structures and the at least one opposed one of the plurality of arm structures away from one another; coupling the at least one of the plurality of arm structures to the first bony structure and the at least one opposed one of the plurality of arm structures to the second bony structure; and releasing the tips of the at least one of the plurality of arm structures and the at least one opposed one of the plurality of arm structures to provide the compressive force between the first bony structure and the second bony structure. Preferably, the tips (and other portions) of the at least one of the plurality of arm structures and the at least one opposed one of the plurality of arm structures are biased towards one another relative to the perpendicular orientation with respect to the body structure such that a desired compressive force is applied to an intercalary structural augment disposed between the first bony structure and the second bony structure. Optionally, the method further includes providing an additional arm structure and an additional opposed arm structure coupled to and extending from the body structure, wherein tips of the additional arm structure and the additional opposed arm structure are biased towards one another relative to the perpendicular orientation with respect to the body structure thereby also providing the compressive force between the first bony structure and the second bony structure. The tips of the at least one of the plurality of arm structures and the at least one opposed one of the plurality of arm structures are biased towards one another relative to the perpendicular orientation with respect to the body structure by a compressive force generated in a proximity of where each of the arm structures and the body structure are coupled. Optionally, the shape memory material includes a shape memory alloy. Optionally, the shape memory alloy includes nitinol. Each of the plurality of arm structures includes a tapered tip such that it may be disposed in a hole drilled into the associated bony structure. Each of the plurality of arm structures further includes one or more friction structures such that it is securely retained in the hole drilled into the associated bony structure. Optionally, the body structure is coupled to the intercalary structural augment disposed between the first bony structure and the second bony structure.

In a further exemplary embodiment, a continuous compression fixation device is provided in which some or all of the plurality of arm structures are replaced with conventional locking or non-locking fixed or variable angle bone screws. The remaining arm structures, if any, operate as before. In the case where all of the arm structures 18 are replaced by bone screws, compressive force is provided solely by the shape memory material body structure itself, which acts on the coupled bony structures through the bone screws.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Figure 1:
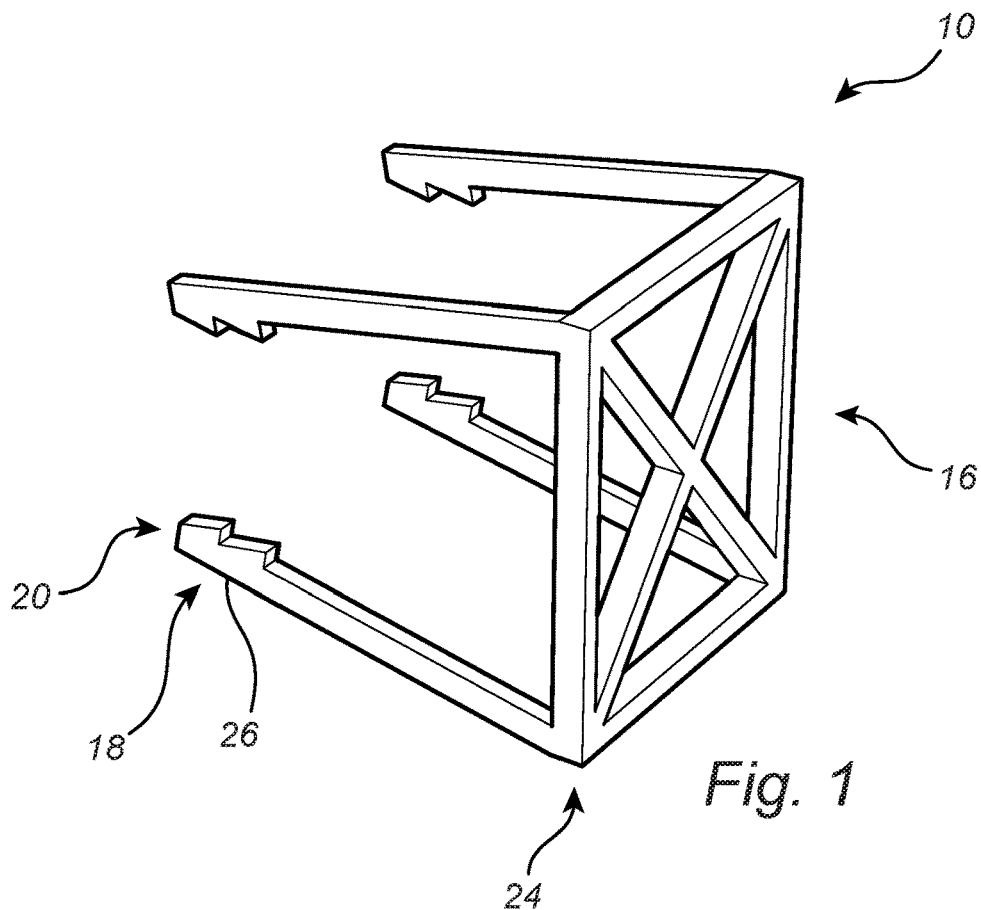
FIG. 1 is a perspective view of one exemplary embodiment of the continuous compression fixation device of the present invention in a deployed configuration.
Figure 2:
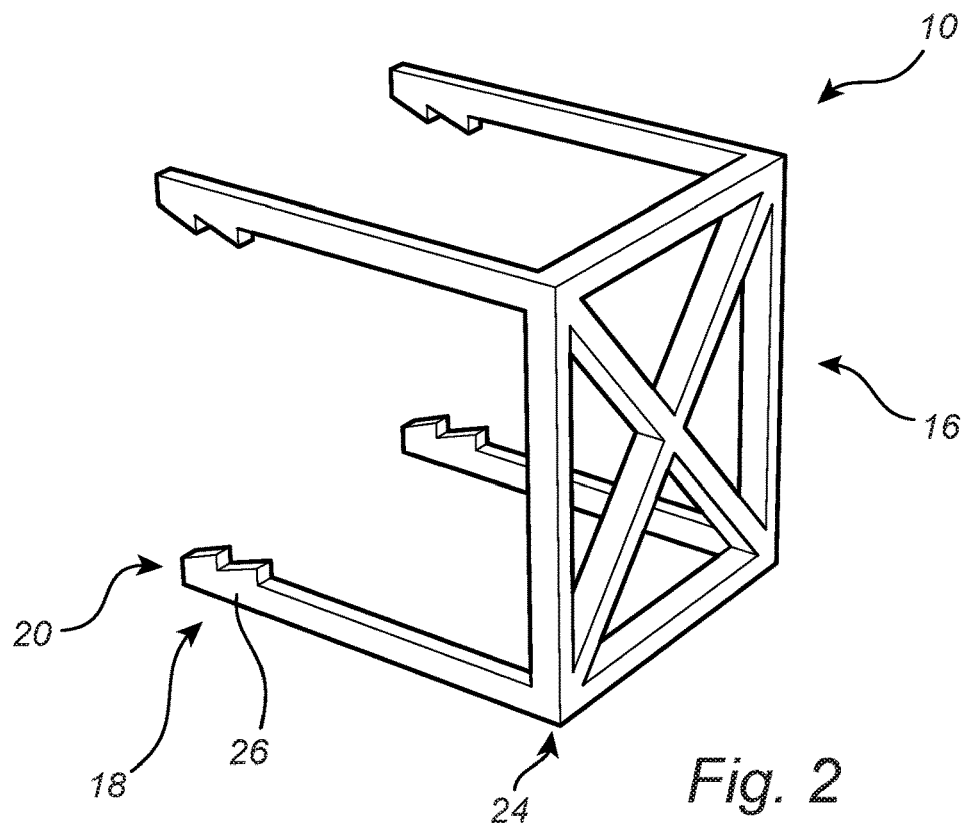
FIG. 2 is a perspective view of one exemplary embodiment of the continuous compression fixation device of the present invention in an expanded configuration.
Figure 3:
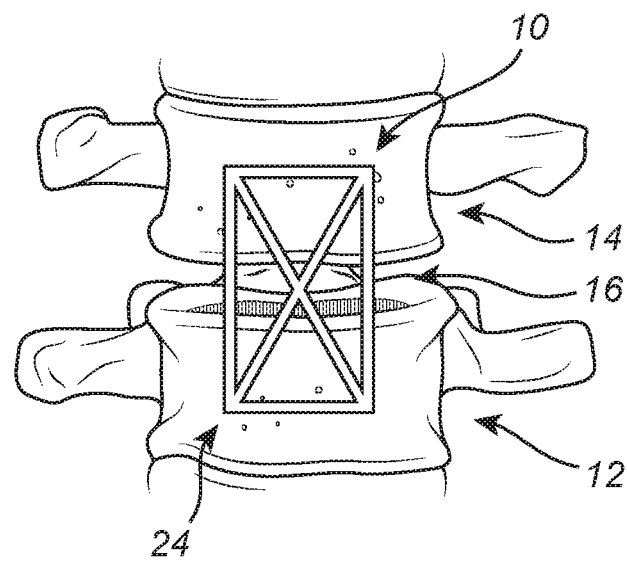
FIG. 3 is a front planar view of one exemplary embodiment of the continuous compression fixation device of the present invention in an implanted and deployed configuration.
Figure 4:
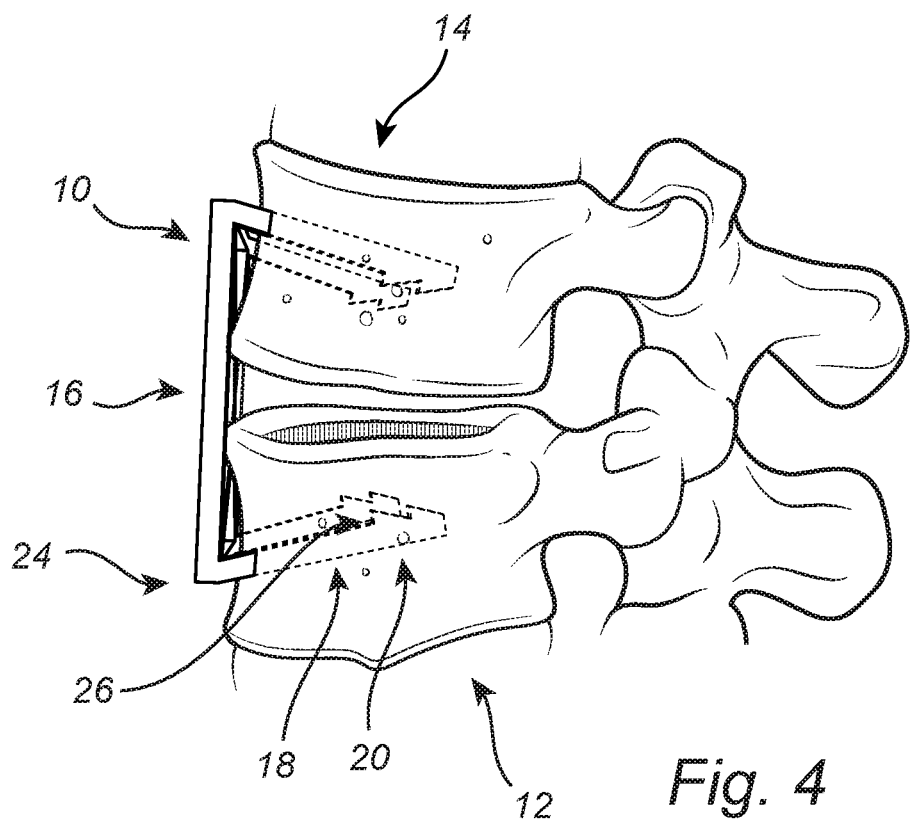
FIG. 4 is a side planar view of one exemplary embodiment of the continuous compression fixation device of the present invention in an implanted and deployed configuration.

Referring now specifically to FIGS. 1-4, in one exemplary embodiment, the present invention provides a continuous compression fixation device 10 for coupling a first bony structure 12 to a second bony structure 14. The continuous compression fixation device 10 includes a body structure 16 and a plurality of arm structures 18 coupled to and extending from the body structure 16 towards the first bony structure 12 and the second bony structure 14. Accordingly, one or more of the plurality of arm structures 18 are configured to be coupled to the first bony structure 12 and one or more of the plurality of arm structures 18 are configured to be coupled to the second bony structure 14. In the exemplary embodiment illustrated, two of the arm structures 18 are associated with each of the bony structures 12 and 14, although other desired numbers of the arms structures 18 could be associated with each of the bony structures 12 and 14 equally.

Figure 6:
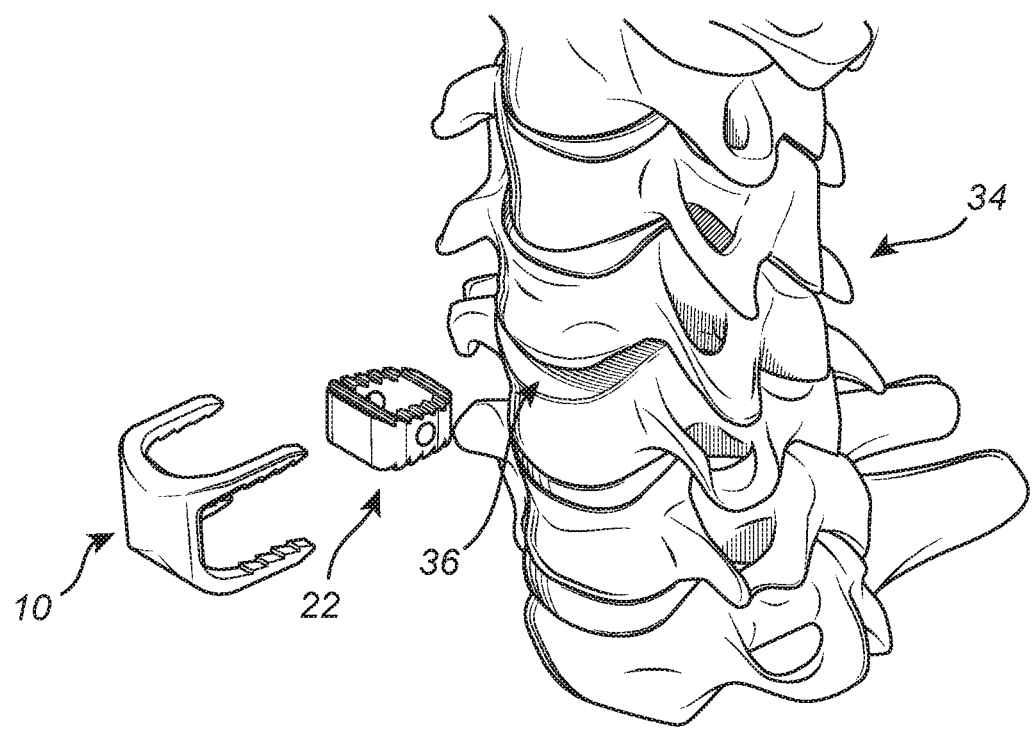
FIG. 6 is a perspective view of one exemplary embodiment of the continuous compression fixation device of the present invention in an expanded configuration being implanted with an intervertebral cage.
Figure 7:
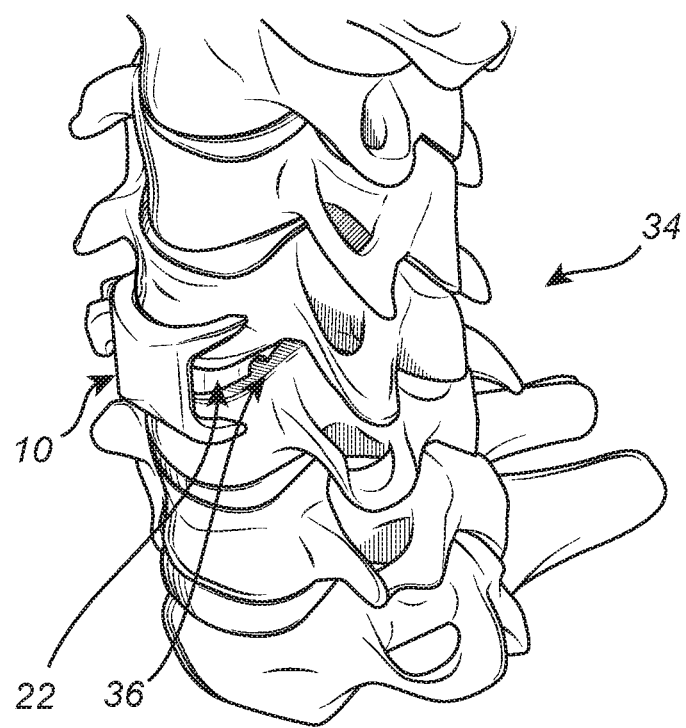
FIG. 7 is a perspective view of one exemplary embodiment of the continuous compression fixation device of the present invention in a deployed configuration implanted with an intervertebral cage.
Figure 8:
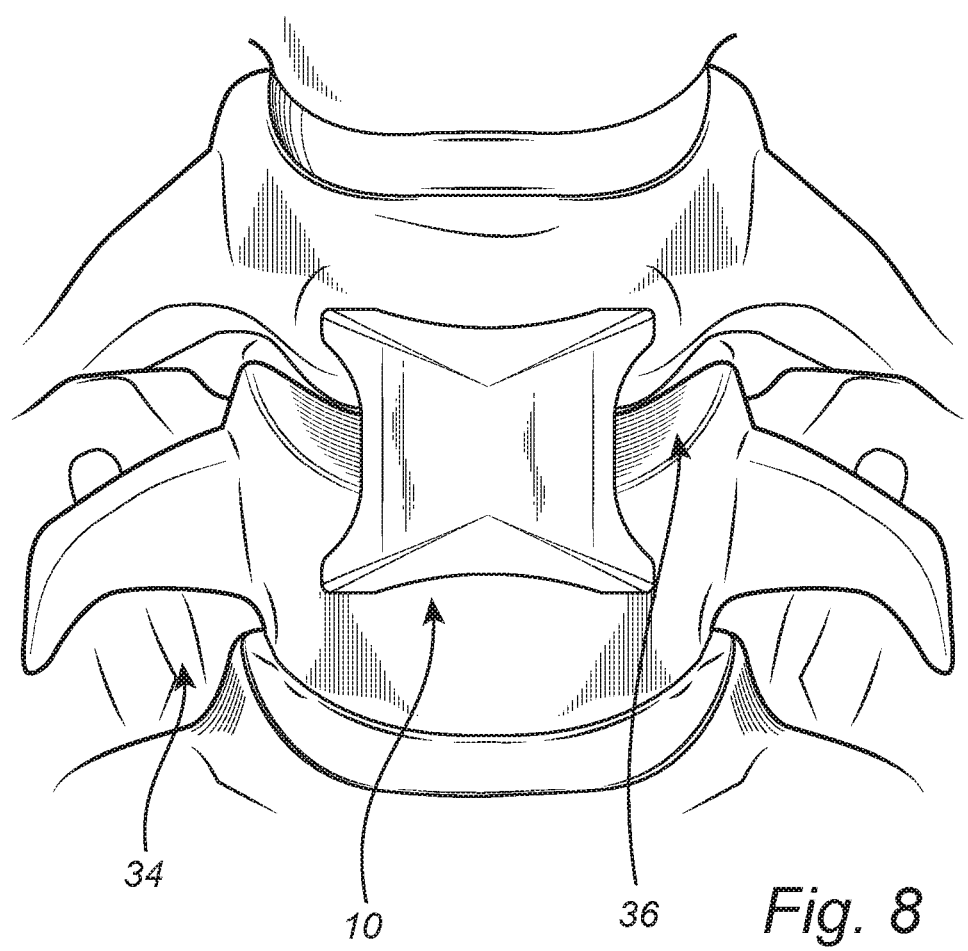
FIG. 8 is a front planar view of one exemplary embodiment of the continuous compression fixation device of the present invention in a deployed configuration implanted with an intervertebral cage.

The body structure 16 and the plurality of arm structures 18 are manufactured from a shape memory material, such as a shape memory polymer or a shape memory alloy like nitinol. It will be readily apparent to those of ordinary skill in the art that any suitable shape memory material may be utilized provided that it continuously biases the structure(s) at issue to an original intended shape after deflection, thereby resisting such deflection with a reactionary force. By design, the tips 20 of the plurality of arm structures 18 are biased towards one another relative to a perpendicular orientation with respect to the body structure 16, thereby providing a compressive force between the first bony structure 12 and the second bony structure 14 when the plurality of arm structures 18 are deflected and coupled to their respective bony structures 12 and 14. In other words, each of the plurality of arm structures 18 is intentionally angled inwards in at least one plane as illustrated and persistently seeks to return to such configuration despite its state of deflection and what it is coupled to. Preferably, by design, the tips 20 of the plurality of arm structures 18 are biased towards one another relative to the perpendicular orientation with respect to the body structure 16 such that a desired compressive force is applied to an intercalary structural augment 22 (FIGS. 6, 7, and 9) disposed between the first bony structure 12 and the second bony structure 14. Again, the tips 20 of the plurality of arm structures 18 are configured to be deflected away from one another prior to being coupled to the first bony structure 12 and the second bony structure 14, respectively. Thus, the plurality of arm structures 18 are opened up prior to implantation into appropriate holes drilled into the first bony structure 12 and the second bony structure 14, for example, and then released subsequent to implantation. This provides a desired compressive force between the first bony structure 12 and the second bony structure 14. This compressive force is applied (and in fact tailored) to the intercalary augment structure 22 disposed between the first bony structure 12 and the second bony structure 14, promoting both fixation and fusion, when appropriate.

The tips 20 (and other portions) of the plurality of arm structures 18 are preferably biased towards one another relative to the perpendicular orientation with respect to the body structure 16 by a compressive force generated primarily in the proximity of where each of the arm structures 18 and the body structure 16 are coupled, at the shoulders 24 of the continuous compression fixation device 10. In general, it is desirable that the body structure 16 and the plurality of arm structures 18 are integrally formed to minimize areas in which failure and corrosion can be initiated and propagate.

Each of the plurality of arm structures 18 includes a tapered and/or sharpened tip 20 such that it may be more easily disposed in the hole drilled into the associated bony structure 12 or 14. Each of the plurality of arm structures 18 further includes one or more friction structures 26 (e.g. protrusions, barbs, or threads) such that it is securely retained in the hole drilled into the associated bony structure 12 or 14.

Figure 5:
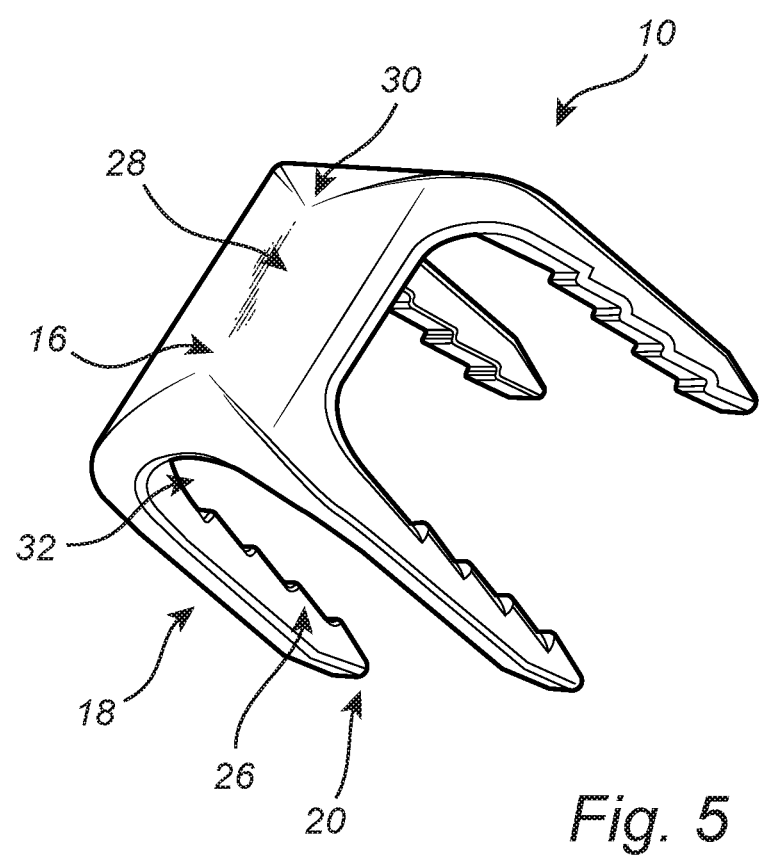
FIG. 5 is a perspective view of one exemplary embodiment of the continuous compression fixation device of the present invention in an expanded configuration.

Referring now specifically to FIG. 5, one exemplary embodiment of the continuous compression fixation device 10 of the present invention is illustrated. In this exemplary embodiment, the body structure 16 is a substantially planar structure 28 with a generally rectangular shape that terminates in a raised central ridge 30 to minimize its anatomical protrusion when the continuous compression fixation device 10 is implanted in a spinal column or the like. The body structure 16 may define any number of recesses, holes, or other openings as desired in a given application. In general, the plurality of arms structures extend away from the body structure 16 at an angle of between greater than about 0 degrees and less than about 45 degrees from perpendicular in a natural or resting state, with a few degrees past zero degrees preferred. This natural or resting angular displacement of the plurality of arm structures 18 is illustrated in one plane along each side of the continuous compression fixation device 10 and not in the perpendicular planes along the ends of the continuous compression fixation device, although such multidimensional angular displacement of the plurality of arm structures 18 is possible. In this exemplary embodiment, each of the plurality of arm structures 18 includes a generally tapered tip 20 for insertion purposes and a plurality of raised barbs 26 for retention purposes. The plurality of arm structures 18 meet the body structure 16 to form a plurality of arcs 32 that are designed to enhance conformal anatomical fit in a given application. As described above, the body structure 16 and the plurality of arm structures 18 are manufactured from a shape memory material, such as a shape memory polymer or a shape memory alloy like nitinol. It will be readily apparent to those of ordinary skill in the art that any suitable shape memory material may be utilized provided that it continuously biases the structure(s) at issue to an original intended shape after deflection, thereby resisting such deflection with a reactionary force. Again, in general, it is desirable that the body structure 16 and the plurality of arm structures 18 are integrally formed to minimize areas in which failure and corrosion can be initiated and propagate.

Figure 9:
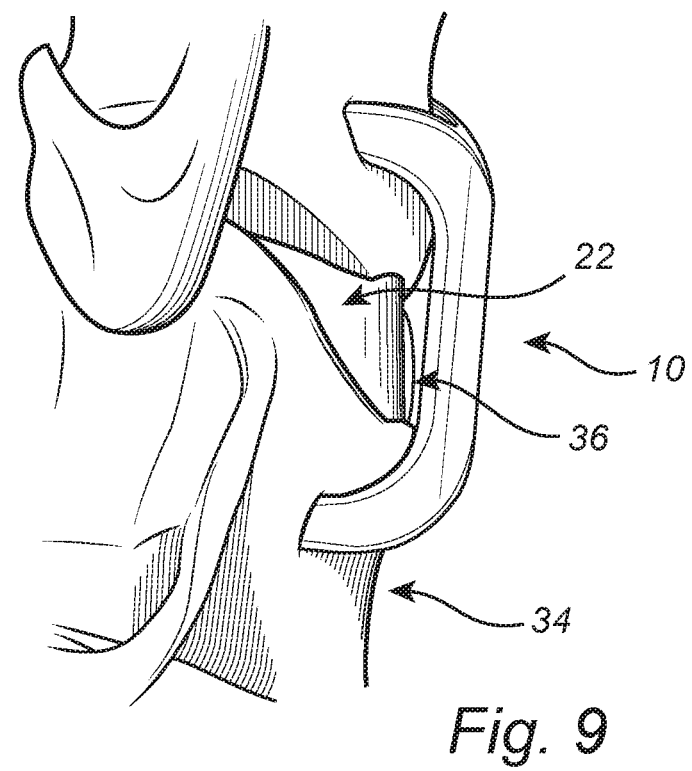
FIG. 9 is a side planar view of one exemplary embodiment of the continuous compression fixation device of the present invention in a deployed configuration implanted with an intervertebral cage.

FIGS. 6-9 illustrate the continuous compression fixation device 10 of the present invention being implanted in a spine 34 of a patient after an intercalary structural augment 22, such as an intervertebral cage and/or bone graft, has been implanted into the prepared intervertebral space 36. FIG. 9 illustrates the low-profile nature of this installation. Although not specifically illustrated, the continuous compression fixation device 10 can be coupled directly to the intercalary structural augment 22, if desired.

Thus, the present invention provides continuous compression across a single-level, or multi-level, osseous segment, with or without the use of an intercalary cage/graft, with fixation using staple arms incorporating, in whole or in part, a shape memory material. The staple is manufactured in a deployed configuration with acute angles between the staple arms. These are heated/expanded and placed into a carrying mechanism, and subsequently deployed into bony structures across the intercalary structural augment. Once deployed, the staple will reconfigure to its original shape, providing continuous compression across the anterior and middle columns of the spine, for example, with most of the compressive force being directed through the middle column through the tips of the staple arms. Compression across the middle column, rather than through an anterior plate, minimizes the concern for iatrogenic kyphosis in the cervical and lumbar spine, for example, and focuses the compression more linearly across the intercalary structural augment.

It is additionally important to consider rotational strain across a fusion mass, just as one would consider resistance to flexion and extension. In that regard, the present invention incorporates a variety of angular connections to resist torsional stresses and provide a lower-strain, higher-stability construct than would typically be seen in existing routine spinal instrumentation after cyclic loading, for example.

Because of the conceptual similarity among all iatrogenic bony fusions, the continuous compression provided by the osseous staple design of the present invention would work for all bony fusions with intercalary structural augments. Other exemplary applications include opening wedge osteotomies with tri-cortical auto/allograft or other material/device osteotomy filling and deformity correction with structural augmentation.

Figure 10:
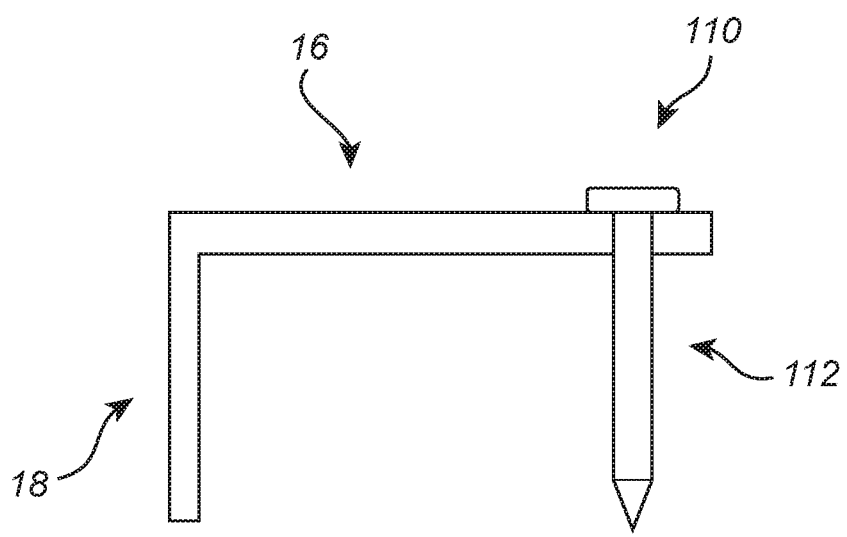
FIG. 10 is a side planar view of another exemplary embodiment of the continuous compression fixation device of the present invention.

Referring now specifically to FIG. 10, in another exemplary embodiment, the present invention provides a continuous compression fixation device 110 in which some or all of the plurality of arm structures 18 are replaced with conventional locking or non-locking fixed or variable angle bone screws 112. The remaining arm structures 18, if any, operate as before. In the case where all of the arm structures 18 are replaced by bone screws 112, compressive force is provided solely by the shape memory material body structure 16 itself, which acts on the coupled bony structures through the bone screws 112.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby for all purposes, and are intended to be covered by the following non-limiting claims.

What is claimed is:

1. A continuous compression fixation system adapted to couple a first bony structure to a second bony structure, comprising:

a body structure comprising four outer edges and four corners;

four arm structures, each arm structure coupled to and extending from the body structure from one of the four corners; and eight arcs, wherein:

each of the eight arcs is formed by one of the four outer edges and one arm structure of the four arm structures;

at least one pair of the four arm structures is adapted to be coupled to the first bony structure and at least one opposed pair of the four arm structures is adapted to be coupled to the second bony structure;

the body structure and the four arm structures are manufactured from a nitinol shape memory alloy;

at least tips of the at least one pair of the four arm structures and the at least one opposed pair of the four arm structures are biased towards one another relative to a perpendicular orientation with respect to the body structure and thereby adapted to provide a compressive force and resist torsional force between the first bony structure and the second bony structure; and the body structure further comprises at least one exterior side surface forming a concave transition between an arm structure of the at least one pair of arm structures and an opposed arm structure of the at least one opposed pair of arm structures.

2. The continuous compression fixation system of claim 1, wherein the at least tips of the at least one pair of the four arm structures and the at least one opposed pair of the four arm structures are biased towards one another relative to the perpendicular orientation with respect to the body structure such that a desired compressive force is applied to an intercalary structural augment disposed between the first bony structure and the second bony structure.

3. The continuous compression fixation system of claim 2, wherein the body structure is coupled to the intercalary structural augment disposed between the first bony structure and the second bony structure.

4. The continuous compression fixation system of claim 1, wherein the at least tips of the at least one pair of the four arm structures and the at least one opposed pair of the four arm structures are adapted to be deflected away from one another prior to being coupled to the first bony structure and the second bony structure, respectively.

5. The continuous compression fixation system of claim 1, wherein the at least tips of the at least one pair of the four arm structures and the at least one opposed pair of the four arm structures are biased towards one another relative to the perpendicular orientation with respect to the body structure by a compressive force generated in a proximity of where each of the four arm structures and the body structure are coupled.

6. The continuous compression fixation system of claim 1, wherein the at least tips of the at least one pair of the four arm structures and the at least one opposed pair of the four arm structures each comprise a tapered tip such that it may be disposed in a hole drilled into the associated bony structure.

7. The continuous compression fixation system of claim 6, wherein each of the four arm structures further comprises one or more friction structures such that it is securely retained in the hole drilled into the associated bony structure.

8. The continuous compression fixation system of claim 1, wherein:

the four outer edges comprise a first outer edge, a second outer edge, a third outer edge, and a fourth outer edge;

the eight arcs comprise a first arc, a second arc, a third arc, a fourth arc, a fifth arc, a sixth arc, a seventh arc, and an eighth arc; and the four arm structures comprise a first arm structure, a second arm structure, a third arm structure, and a fourth arm structure, wherein:

the first arc is formed by the first outer edge and the first arm structure;

the second arc is formed by the second outer edge and the first arm structure;

the third arc is formed by the second outer edge and the second arm structure;

the fourth arc is formed by the third outer edge and the second arm structure;

the fifth arc is formed by the third outer edge and the third arm structure;

the sixth arc is formed by the fourth outer edge and the third arm structure;

the seventh arc is formed by the fourth outer edge and the fourth arm structure; and the eighth arc is formed by the first outer edge and the fourth arm structure.

9. The continuous compression fixation system of claim 1, wherein the continuous compression fixation device further comprises an intercalary structural augment for insertion between the first bony structure and the second bony structure.

10. A continuous compression fixation system adapted to couple a first bony structure to a second bony structure, comprising:

an intercalary structural augment for insertion between the first bony structure and the second bony structure;

a body structure comprising four outer edges and four corners;

four arm structures, each arm structure coupled to and extending from the body structure from one of the four corners; and eight arcs, wherein:

each of the eight arcs is formed by one of the four outer edges and one arm structure of the four arm structures;

the four arm structures are adapted to couple the body structure to the first bony structure and the second bony structure, respectively;

the body structure and the four arm structures are manufactured from a nitinol shape memory alloy; and the shape memory material is adapted to provide a compressive force and resist a torsional force between the first bony structure and the second bony structure when the body structure and the four arm structures are deflected from a first configuration to a second configuration and subsequently released.

11. The continuous compression fixation system of claim 10, wherein the compressive force is applied to the intercalary structural augment disposed between the first bony structure and the second bony structure.

* * * * *